United States Patent [19]

Fehrenbach

[11] 4,389,136

[45] Jun. 21, 1983

[54] METHOD OF DETERMINING DENSITY

[75] Inventor: Robert J. Fehrenbach, Wauwatosa, Wis.

[73] Assignee: Seaman Nuclear Corporation, Milwaukee, Wis.

[21] Appl. No.: 227,913

[22] Filed: Jan. 23, 1981

[51] Int. Cl.³ .................... E01C 7/18; E01C 23/00
[52] U.S. Cl. .................................. 404/75; 250/308
[58] Field of Search ............... 404/113, 117, 75, 72, 404/83; 250/308

[56] References Cited

U.S. PATENT DOCUMENTS

| | | | |
|---|---|---|---|
| 2,897,734 | 8/1959 | Bodine | 404/75 |
| 3,252,389 | 5/1966 | Gardner | 404/75 |
| 3,599,543 | 8/1971 | Kerridge | 404/117 |
| 4,079,237 | 3/1978 | Schlesinger | 250/308 X |
| 4,113,403 | 9/1978 | Tertinek | 404/113 |
| 4,140,906 | 2/1979 | Morrison | 250/308 |

*Primary Examiner*—Nile C. Byers, Jr.
*Attorney, Agent, or Firm*—Fred Wiviott

[57] ABSTRACT

An in situ non destructive method employing a radiation device to rapidly determine the density of very thin top layers of material independently of the underlying base material comprising of the steps of: measuring the density $D_b$ of the base layer with an radiation measuring device, determining the thickness t of the top layer, measuring the density $D_g$ of the composite with the radiation measuring device, and determining the density of the top layer from the expression:

$$D_t = D_b + \frac{D_g - D_b}{1 - e^{-t/k}}$$

where k is a constant.

4 Claims, 3 Drawing Figures

METHOD OF DETERMINING DENSITY

BACKGROUND OF THE INVENTION

This invention relates to density determination and more particularly, to the in situ density measurement of a layer of material disposed on a base layer.

In certain paving operations, very thin layers of asphaltic concrete are overlayed on an existing roadway or base as a wear course. Construction machinery employed in the application of such overlays, which are often as thin as 0.7 inches, are generally constructed and arranged for providing a generally planar upper surface. This can result in thickness and density variations since the underlying surface is likely to be uneven. It is, therefore, desirable to accurately determine the density of such top layers as they are applied so that adjustments can be made to thereby minimize the formation of surface variations which would otherwise result from heavy traffic compressing the thicker and generally less dense portions of the layer.

Present density radiation devices tend to "read" through the thin top layer providing a density measurement that is a composite of the top layer and underlying base courses. As a result, such density measurements are not satisfactory for determining if the compacted top layer conforms to design specifications. It is, therefore, desirable to provide a method for rapidly and accurately determining the density of the applied layer so that correction in the compacting operation can be made thereby minimizing the possibility that costly reworking of the entire paving operation may be required.

SUMMARY OF THE INVENTION

It is an object of the invention to provide a new and improved method of measuring density.

A more specific object of the invention is to provide a new and improved method of the in situ measurement of a top layer of material superimposed on a base layer.

A further object of the invention is to provide a method of measuring the density of the layer of paving material as the same is being applied to a base layer to permit adjustment of the layer application apparatus.

These and other objects and advantages of the present invention will become more apparent from the detailed description thereof taken with the accompanying drawings.

DETAILED DESCRIPTION OF THE PREFERRED EMBODIMENT

Figure 1:
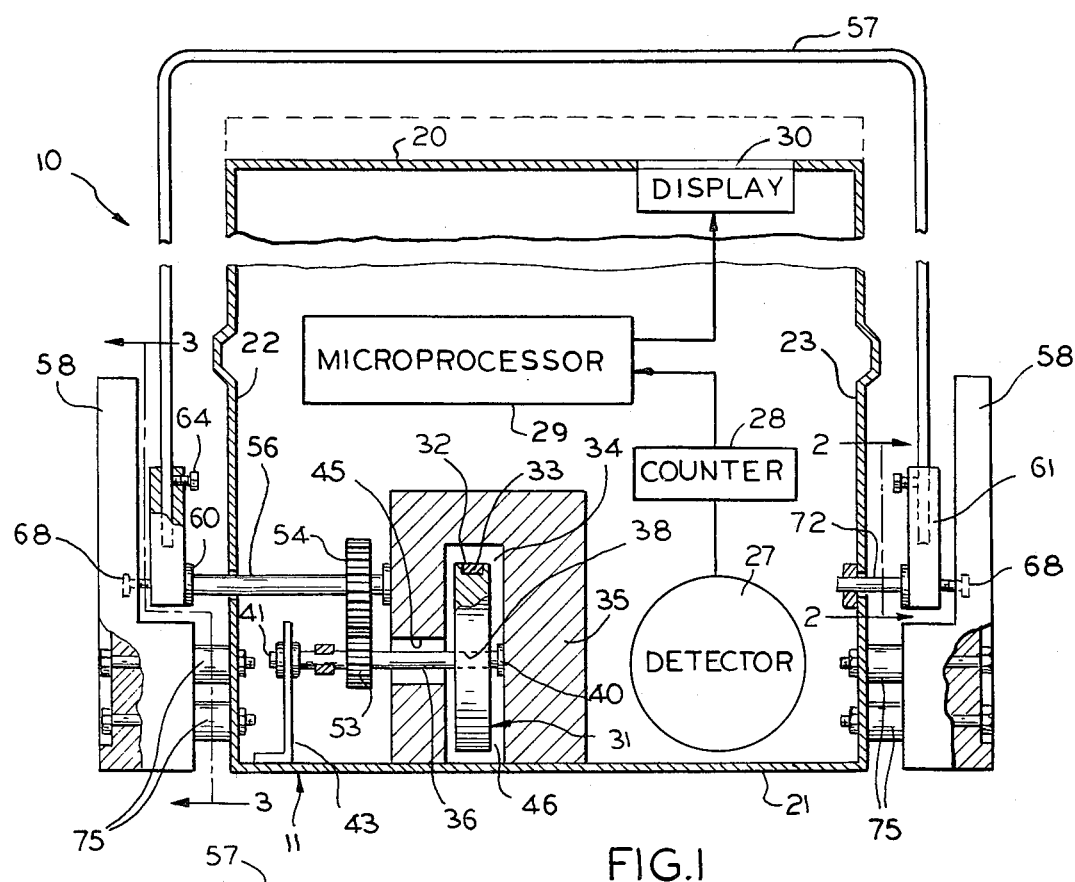
FIG. 1 schematically illustrates a density measuring meter which may be used to perform the method of the invention.

The preferred embodiment of the invention will be described in relation to the air-backscatter radiation measuring device illustrated schematically in the drawings. For a more complete description of this device, reference is made to U.S. Pat. No. 4,140,906. In particular, a density measuring apparatus 10 is shown to include a housing 11 which is generally rectangle in vertical and horizontal cross sections and includes a top wall 20, a bottom wall 21 and end walls 22 and 23. The housing 11 is preferably constructed of aluminum, plastic or other suitable materials which provides the desired strength but which freely pass the photons employed for the density measurements. Adjacent the right side of housing 11 as viewed in the drawing, a radiation detection system is schematically shown to include a geiger tube 27 which is sensitive to photons and a counter 28 for totaling the photon sensed by tube 27. A microprocessor 29 is connected to the counter 28 and to a display 30. The detector 27, the counter 28, the microprocessor 29 and the display 30 are all well known in the art and, therefore, will not be discussed in greater detail for the sake of brevity.

A source wheel 31 is mounted for rotation within housing 11 and generally comprises a disc-like member having a recess 32 in its periphery for receiving a radioactive source 33. The wheel 31 is mounted for rotation about a generally horizontal axis within a recess 34 formed in a barrier 35 mounted in the bottom wall 21 of housing 11. More particularly, wheel 31 is affixed to a shaft 36 which extends through an axial bore 38 and whose opposite ends are journaled for rotation in aligned bearings 40 and 41 affixed, respectively, within recess 34 and to an L-shaped bracket 43 extending upwardly from and affixed to the bottom wall 21. Both wheel 31 and barrier 35 are formed of a suitable material, such as lead, and barrier 35 completely surrounds wheel 31 except for an axial opening 45 which permits passage of shaft 36 and a bottom opening 46 adjacent the lower periphery of wheel 31. When the wheel 31 is in its inoperative position shown in the drawings so that the source 33 is adjacent the upper end of recess 34, both an operator and the detector 27 will be shielded from the source 34. When the wheel 31 is rotated 180° to its operative position as will be discussed more fully below, the source 33 will be adjacent the opening 45. However, the shield 35 will still protect an operator as well as the detector 27 from direct radiation.

Wheel 31 may be rotated in any conventional manner such as by means of a first gear 53 mounted on shaft 36 and a second gear 54 which meshes with gear 53 and is mounted on a second shaft 56 journaled for rotation about an axis parallel to shaft 36. The gears 53 and 54 may be rotated by means of a handle 57 which is also coupled to a pair of end plates 48 which in turn are coupled to housing 11 whereby the housing may be moved between its contact position shown by full lines in FIG. 1 and an elevated air gap position shown by broken lines.

Figure 2:
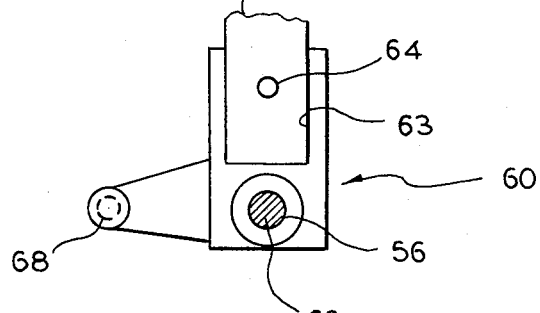
FIG. 2 is a view taken along lines 2—2 of FIG. 1.
Figure 3:
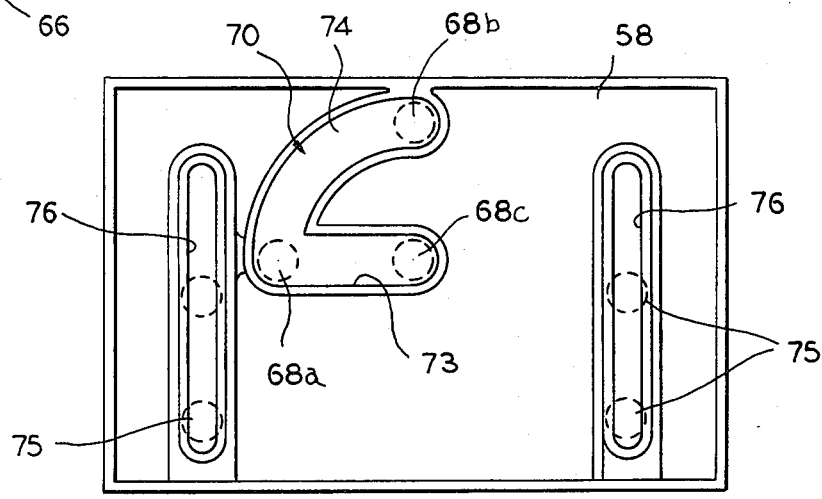
FIG. 3 is a view taken along lines 3—3 of FIG. 1.

More specifically, the handle 57 is coupled to the housing 11 and to the end plates 58 by means of a pair of L-shaped arms 60 and 61, only one of which is shown in FIG. 2 but which are mirror images of each other. The arm 60 includes a recess 63 formed in one end thereof for receiving the end of handle 57 which is secured therein by means of a set screw 64. At the elbow of arm 60 is a socket 66 for receiving the end of shaft 56 after the latter has passed through housing wall 22. The other end of arm 60 has a stud 68 extending normally therefrom for being received in a generally C-shaped slot 70 formed in end plate 60. The other end of handle 57 is similarly secured to the L-shaped arm 64 which is coupled at its elbow by stub shaft 72 to the end wall 23 of housing 11 and to a shaped slot in end wall 58 which is identical to the slot 70 but a mirror image thereof. As seen in FIG. 3, the slot 70 has a horizontal section 73 and an arcuate, generally vertical section 74. Two pairs of studs 75 are affixed to each side wall 22 and 23 of housing 11 and in general parallelism and the other end of each pair are received within vertical slots 76 formed in the adjacent end member 58 as shown in FIG. 3.

As discussed more fully in U.S. Pat. No. 4,140,906, when the wheel 31 is in its position shown in FIG. 1, each of the studs 68 will be at the knee of their associated slot 70 and the housing 11 will be in a contact position shown by full lines in FIG. 1. When the handle 57 is rotated 90° clockwise in a forward direction, the wheel 31 will rotate 180° to move the source 33 adjacent the lower opening 46. This will also rotate the arms 60 and 64 so that the studs 68 will move from their positions indicated by the reference numeral 68a to the position indicated by reference numeral 68b. Because the arm 64 is free to rotate in this manner, the housing 11 will remain in its contact position and a contact reading can be taken by detector 21. When an air gap reading is desired, handle 57 is first returned to its vertical position so that the studs 68 will again return to the knees of their associated slots 70. Further rotation of the arm 57 in the opposite direction, however, will force the studs 68 to move from the position shown by reference numeral 68a to the position shown by reference numeral 68c. As a result, the housing 11 will be moved upwardly to its air gap position shown by broken lines in FIG. 1 as the studs 74 slide upwardly in slots 76. The wheel 31 will also have rotated to reposition the source adjacent opening 46 to permit an air gap reading to be taken.

When a layer of asphalt, for example, is being applied to a base layer of another material, such as concrete, it is common to employ a device, such as a vibratory compactor, which is preset to apply material of a predetermined thickness. In order to achieve the desired density, the asphaltic material must be compacted by making a number of passes over the asphalt layer with a heavy roller, for example. However, because of variables, such as temperature, the surface to which the material is being applied, the frequency of vibration of the compactor and the number of roller passes, actual density may vary. The density measuring apparatus shown in FIG. 1 can be employed to determine density in accordance with the method of the invention so that rapid adjustments can be made to insure compliance with specifications.

More specifically, the thickness t of the top layer of material is first determined from the specifications and that information is provided to the microprocessor 29. The microprocessor will also be provided with an instrument constant which is determined when the device is manufactured and which will depend upon the nature and strength of the source, the geometry of the apparatus and the sensitivity of the detector 27 and will vary slightly from instrument to instrument.

Before the layer of material whose density is to be measured is applied, the density measuring device 10 will first measure the density of the sub-layer at one or more locations by taking both contact and air gap measurements. This information will be delivered to the microprocessor which will determine density of the sub-layer in the manner discussed in U.S. Pat. No. 4,140,906. After the material laying apparatus has applied the surface layer and the same has been compacted by a roller, a second group of density measurements are taken at the same locations. Again, these will include contact and air gap measurements. This information will also be provided to the microprocessor which will then determine the density of the top layer from the following expression:

$$D_t = D_b + \frac{D_g - D_b}{1 - e^{-t/k}}$$

where
$D_t$ equals the density of the top layer;
$D_b$ equals the density of the base layer;
$D_g$ equals the density measured by the instrument after the application of the top layer;
t equals the predetermined thickness of the top layer; and
k equals the instrument constant.

The density of the top layer of material will be indicated in digital or analog form in the readout 30. In this manner, the operator can make periodic adjustments in the material application or vary the number of roller passes to increase or decrease the density of the material being applied in accordance with any deviation of the indicated density from the specification. In a typical application, the measurements would be made after a few roller passes so that the minimum number of passes consistant with the desired density could be determined.

For example, assume a layer of asphalt may be applied to compacted soil. A typical density reading for compacted soil is 116 lbs/ft$^3$. This would be determined by the microprocessor on the basis of contact and air measurements. A one inch layer of asphalt is applied and compacted by a roller. A composite density reading is then taken, such as 142 lbs/ft$^3$. With an instrument constant k of 0.64, the density of the asphalt layer would be $$D_t = 116 + \frac{142 - 116}{1 - e^{-1/.64}}$$

$$D_t = 148.9$$

This would be close to a typical specification. However, if the density does not meet the specifications, additional roller passes can be made.

In another example, the asphalt is applied to a layer of worn concrete. Here the base layer measurement would be about 155 lbs/ft$^3$ and the composite reading with a one inch top layer would be about 150. The density of the top layer would then be $$D_t = 155 + \frac{150 - 155}{1 - e^{-1/.64}}$$

$$D_t = 148.7$$

While only a single embodiment of the invention has been illustrated and described, it is not intended to be limited thereby, but only by the scope of the appended claims. In addition, while the method of the invention has been illustrated and described in relation to a particular type of radiation measuring device, this is merely intended as an example, it being appreciated that the method may also be employed with other radiation density measuring devices as well.

I claim:

1. A paving method wherein a top layer of paving material is applied to a base layer,
determining the density $D_b$ of the base layer, applying a top layer of paving material to the base layer and compacting the top layer, determining the composite density $D_g$ of the compacted top layer and base layer, determining the density $D_t$ of the top layer from the expression $$D_t = D_b + \frac{D_g - D_b}{1 - e^{-t/k}}$$

where t is the thickness of the top layer; and k is an instrument constant.

2. The method set forth in claim 1 wherein said top layer is further compacted if the density thereof falls below a predetermined value.

3. A method of determining the density of a top layer of asphaltic paving material which is compacted by a roller, said top layer being disposed on a base layer of a second material comprising the steps of:

determining the density $D_b$ of the base layer prior to the application of the top layer, determining the composite density $D_g$ of the top layer and base layer after the application of the top layer, determining the density $D_t$ of the top layer from the expression $$D_t = D_b + \frac{D_g - D_b}{1 - e^{-t/k}}$$

where t is the thickness of the top layer; and k is an instrument constant, said density $D_t$ indicating the need for further rolling.

4. The method set forth in claim 3 wherein said density measurements are made with a backscatter radiation measuring device.

* * * * *